United States Patent [19]

Bornengo et al.

[11] 4,083,900

[45] Apr. 11, 1978

[54] CONTINUOUS PROCESS FOR THE PREPARATION OF N-MONOMETHYLAMIDE OF O,O-DIMETHYL-DITHIOPHOSPHORYL ACETIC ACID

[75] Inventors: Mario Bornengo, Massa; Saverio Grego, Mestre (Venice); Sergio Serdi, Milan, all of Italy

[73] Assignee: Montedison S.p.A., Milan, Italy

[21] Appl. No.: 741,990

[22] Filed: Nov. 15, 1976

Related U.S. Application Data

[63] Continuation-in-part of Ser. No. 560,114, Mar. 20, 1975, abandoned.

[30] Foreign Application Priority Data

Dec. 3, 1974  Italy .............................. 30137 A/74

[51] Int. Cl.$^2$ ............................................. C07F 9/165
[52] U.S. Cl. .................................... 260/984; 260/943
[58] Field of Search .......................................... 260/984

[56] References Cited

FOREIGN PATENT DOCUMENTS

2,500,452  7/1975  Germany .............................. 260/984

*Primary Examiner*—Anton H. Sutto

[57] ABSTRACT

The N-monomethylamide of O,O-dimethyl-dithiophosphorylacetic acid is prepared continuously, in the form of essentially pure, beautiful colorless crystals, by reacting the methyl ester of O,O-dimethyldithiophosphoryl acetic acid with a 34% aqueous solution of methylamine ($CH_3NH_2$) at a temperature between 0° C and 10° C, in water containing a surfactant which is an alkyl sulphonate or an alkylarylsulphonate and, as an essential feature of the process, recycling, back to the reaction vessel, from 1/10 to 1/20 of the slurry obtained as a result of the reaction between the methyl ester of O,O-dimethyl-dithiophosphorylacetic acid and the 34% solution of $CH_3NH_2$.

3 Claims, No Drawings

CONTINUOUS PROCESS FOR THE PREPARATION OF N-MONOMETHYLAMIDE OF O,O-DIMETHYL-DITHIOPHOSPHORYL ACETIC ACID

This application is a continuation-in-part of our application Ser. No. 560,114, filed Mar. 20, 1975 now abandoned.

THE PRIOR ART

Italian Pat. No. 661,487, assigned to Montedison, describes a process for obtaining the N-monomethylamide of O,O-dimethyl-dithiophosphorylacetic acid by reacting the methyl ester of O,O-dimethyl-dithiophosphorylacetic acid with methylamine, wherein the temperature is maintained constant by the addition of substances boiling at temperatures comprised between $-15°$ C and $+10°$ C, and which do not react with either the methyl ester or the methylamine, or with the N-monomethylamine produced.

For this purpose, there was used butane (b.p. $0.6°$ C); $CCl_2F$—$CF_3$ (b.p. $-2°$ C); a mixture of 79.5% of $CCl_3F$ and 20.5% of $CCl_2F_2$ (b.p. $2°$ C); methylcyclopropane (b.p. $-1.5°$ C at 5 atm.) etc.

The product obtained under those conditions is very pure and well crystallized. However, the conditions are rather burdensome in practice, inasmuch as it is necessary either to carry out the condensation in a closed environment under superatmospheric pressure or use an effective refrigerating system for hindering evaporation of the added substance boiling at $-15°$ C to $+10°$ C. Moreover, under those practical restrictions, the process is not adapted to production of the desired N-monomethylamide on a continuous scale.

THE PRESENT INVENTION

An object of this invention is to provide an improved, continuous process for the preparation of the N-monomethylamide of O,O-dimethyl-dithiophosphorylacetic acid which does not have the disadvantages mentioned, in practice.

We have found that this and other objects are accomplished by a process which gives end results which are altogether equal to those obtained by the process of Italian Pat. No. 661,487, and in accordance with which the reaction between O,O-dimethyl-dithiophosphorylacetic acid and methyl amine is carried out at a temperature of from $0°$ C to $10°$ C in water containing a surfactant which is an alkyl sulphonate or an alkylarylsulphonate, and from 1/10 to 1/20 of the resulting slurry is recycled to the reaction vessel.

The surface active agent, in addition to facilitating interpenetration of the two phases (the methyl ester of O,O-dimethyl-dithiophosphorylacetic acid and the aqueous solution of monomethylamine) has the property of maintaining some organic impurities in emulsified condition, including the methyl ester itself, the trimethylester

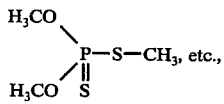

and some ionic impurities (quaternary salts of ammonium) which would otherwise be included in the N-methylamide of O,O-dimethyl-dithiophosphorylacetic acid and render it more noxious, greasy to the touch and difficult to stockpile.

The alkyl sulphonates and alkylarylsulphonates which have given excellent results in the practice of the present process are the product marketed as "Secapur" by Busing Fasch (and which consists of 60% sodium n-alkylsulphonate, plus 26% polyoxymethylene glycol, plus 14% $H_2O$), and "Alarsol 2P", marketed by Montedison (and which consists of 28% sodium dodecylbenzene sulphonate, 60% sodium sulphate, and 12% polyphosphate).

By using the surface active agents indicated, the reaction time is considerably shortened.

Recycling from 1/10 to 1/20 of the slurry is essential because is not only serves to accelerate the reaction but removal of the impurities present is achieved by the combined effect of the recycling and the alkylsulphonate or alkylarylsulphonate present in the reactor, with the unpredictable and unexpected result that recycling of part of the impure slurry from which the reaction product was precipitated, to the impure solution yields a new crop of the same reaction product which has a higher degree of purity than the preceding crop.

Both conditions are required to achieve the foregoing result, that is, use of the alkyl sulphonate or alkylarylsulphonate and recycling 70 l/hr of the slurry to the solution in which the reaction occurs.

Thus, it has been established that when the reaction between the ester and amine is carried out in the presence of "Alarsol" but without recycling of part of the slurry, the yield falls to 86–87% of a product having:

| | |
|---|---|
| melting point | 48 – 49° C |
| purity (as N-methylamide of O,O-dimethyldithiophosphoryl acetic acid | 97.5 – 97.8% |
| impurities | |
| (a) dithiophosphoric acid trimethylester | 0.4 – 0.6% |
| (b) O,O-dimethyldithio-phosphorylacetic acid monomethyl ester | 1.0% |
| water | 0.4% |

In contrast, under the conditions of the present example, combining use of the "Alarsol" with recycle of part of the impure slurry to the impure reaction solution, the yield increases to 88–90% of crystals having the characteristics shown in the following example.

It has also been established that using other surfactants, such as sodium dodecylbenzensulphonate (product of the Society KEK) and sodium oleyloxyethansulphonate, without recycle of the part of the slurry to the reaction solution, the results achieved by the present process are not achieved. Such results are only achieved when the particular surfactants which are alkylsulphonates or alkylarylsulphonates are used in combination with recycle of part of the slurry. This is surprising since it could not be expected that a new crop of a same product precipitated from a mother liquor containing impurities, and to which a mother liquor from which one crop of the product has been separated, and also containing impurities, would have a higher degree of purity than the preceding crop, impurities having been added to impurities.

The following example is given to illustrate the process of this invention in more specific detail.

EXAMPLE I

Into a 4 liters reactor, cooled down to 0° C, fitted with a stirrer, there were continuously and contemporaneously fed:

| | |
|---|---|
| a 34% CH$_3$NH$_2$ solution | at 208.32 g/hr |
| methyl ester of O,O-dimethyl-dithiophosphorylacetic acid | at 425.9 g/hr |
| water containing 3.3% of "Alarsol 2P" | at 352.7 g/hr |

The reactor, through a collector pipe for the overflow slurry, was connected to a centrifuge for the recovery of the crystals; a portion of the slurry obtained was recycled to the reactor, by means of a pump, through a shunting valve comprised in the pipe between the centrifuge and reactor. The dwelling time was 3 hours; the recycling rate of the slurry was 60–80 l /hr.

The crystal cake obtained in the centrifuge (rotating at 2000 r.p.m., synthetic fiber filter) was washed first with water containing 0.2% of "Alarsol" at 0° C (ratio water/crystals = 0.4) recycling the outflowing water thrice, then washing with deionized water (ratio crystals/water = 0.8).

The cake was then dried in a normal way in the air.

Thereby were obtained 365 g/hr of fine crystals of N-methylamide of O,O-dimethyl-dithiophosphorylacetic acid, which were colorless, odorless and has a m.p. = 50° C. The crystals were of the following composition:

| | |
|---|---|
| n-methylamide | 99. % |
| trimethylester of dithiophosphoric acid | 0.2% |
| methyl ester of O,O-dimethyldithio-phosphorylacetic acid | 0.4% |
| H$_2$O | 0.4% |

The yield on the starting methyl ester of O,O-dimethyl-dithiophosphorylacetic acid was 88–90%.

EXAMPLE II

Under the same conditions of Example I, by feeding into the reactor along with the solution of 34% of monomethylamine (208.32 g/hr) and O,O-dimethyldithiophosphorylacetic acid methyl ester (425.9 g/hr), 352.7 g/hr of water containing 1% of:

1. Sodium dodecylbenzensulphonate (sold by Society KEK; 1% of such surfactant corresponds to the quantity of sodium dodecylbenzensulphonate contained in 3% of "Alarsol").
2. Sodium oleyloxiethansulphonate (corresponding to the quantity of dodecylbenzensulphonate contained in 3% of "Alarsol")

and recycling 70 l/hr of the slurry to the reactor, the yields are in the former case of 90% in the latter of 89% and the products obtained have the following composition and characteristics:

| | with dodecyl benzensulphonate | with oleyloxi-ethan-sulpho-nate |
|---|---|---|
| Melting point | 50° C | 50° C |
| O,O-dimethyldithiopho-sphorylacetic acid monomethylamide | 99 | 99 |
| Ditiophoshoric acid trimethylester | 0,15 | 0,25 |
| O,O-dimethyldithiopho-sphorylacetic acid methyl ester | 0,42 | 0,35 |
| H$_2$O | 0,4 | 0,4 |

We claim:

1. A continuous process for the preparation of N-monomethylamide of O,O-dimethyl-dithiophosphorylacetic acid in the form of essentially pure, colorless crystals and in high yield, which process comprises reacting the methyl ester of O,O-dimethyldithiophosphorylacetic acid with an aqueous solution of monomethylamine and is further characterized by the following combination of conditions: (a) the reaction of the methyl ester and methylamine is effected in the presence of an anionic surfactant which is an: aqueous mixture of sodium n.alkylsulphonate plus polyoxymethyleneglycol or a mixture of sodium dodecylbenzene sulphonate, sodium sulphate and polyphosphate, and (b) from 1/10 to 1/20 of the reaction slurry is recycled to the solution in which the reaction occurs.

2. The process of claim 1 in which the surfactant is a mixture of 60% sodium n-alkylsulphonate, plus 26% of polyoxymethylene glycol, plus 14% of H$_2$O.

3. The process of claim 1, in which the surfactant is a mixture of 28% sodium dodecyl benzene sulphonate, 60% sodium sulphate, and 12% polyphosphates.

* * * * *